US00PP18998P3

(12) United States Plant Patent
Smith

(10) Patent No.: US PP18,998 P3
(45) Date of Patent: Jul. 1, 2008

(54) ***HIBISCUS* PLANT NAMED 'JODI'**

(50) Latin Name: *Hibiscus syriacus*
Varietal Denomination: Jodi

(75) Inventor: David Smith, Powell, OH (US)

(73) Assignee: J & D Smith Enterprises, Inc., Powell, OH (US)

( * ) Notice: Subject to any disclaimer, the term of this patent is extended or adjusted under 35 U.S.C. 154(b) by 0 days.

(21) Appl. No.: 11/480,005

(22) Filed: Jun. 30, 2006

(65) Prior Publication Data

US 2008/0005818 P1 Jan. 3, 2008

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
(74) *Attorney, Agent, or Firm*—Gallagher & Dawsey Co, LPA; Michael J. Gallagher; David J. Dawsey

(57) ABSTRACT

A new cultivar of *Hibiscus, Hibiscus syriacus* 'Jodi,' characterized by three color irregular variegation (Dark green, light green, and golden yellow); a large, pure white flower; a longer blooming duration; two additional seasons of ornamental qualities because of variegated leaves; and triploid (sterile) genetic character.

1 Drawing Sheet

LATIN NAME OF THE GENUS AND SPECIES OF THE PLANT CLAIMED

Botanical classification: *Hibiscus syriacus.*
Varietal denomination: 'Jodi'.

BACKGROUND OF THE INVENTION

*Hibiscus syriacus* 'Jodi' is a new cultivar of the common Rose-of-Sharon. The plant will be useful as an improved ornamental *Hibiscus*. The plant has irregular variegation of yellow and green which provides enhanced spring and summer ornamental characteristics. The plant also has sterile, single, white flowers which in late summer provide a longer duration of flowering than other *Hibiscus* known to the inventor. *Hibiscus syriacus* 'Jodi' is hardy from Zone 5 to Zone 8. The plant can be used as a specimen, in borders, as a hedge, or as a small tree.

The origin of *Hibiscus syriacus* 'Jodi' is a spontaneous, naturally occurring genetic branch mutation from *Hibiscus syriacus* 'Diana'. The discovery was made at Smiths Gardens; a wholesale nursery located in Worthington, Ohio. The mutation has been propagated asexually by softwood cuttings and observed in numerous controlled environments to test for stability, hardiness, vigor, and disease and insect resistance. Clones or propagules of the claimed plant are identical to the original plant in all distinguishing characters, demonstrating that the claimed plant is stable.

SUMMARY OF INVENTION

Novel characteristics—as compared to 'Diana'

1. Three color irregular leaf variegation (Dark green, light green, and golden yellow)

Novel characteristics—as compared to all other *Hibiscus* known to the inventor

1. Triploid (sterile)
2. Large, pure white, single flower
3. Longer blooming duration 4. Two additional seasons of ornamental qualities because of variegated leaves.

BRIEF DESCRIPTION OF THE PHOTOGRAPHS

Without limiting the scope of the present invention as claimed below and referring now to the drawings and figures:

FIG. 1 is a close up view of the leaves of 'Jodi.' The colors in the photographs are as close as possible with the photographic and printing technology utilized. The color values cited in the detailed botanical description accurately describe the color of the new *Hibiscus*.

DETAILED BOTANICAL DESCRIPTION OF THE PLANT

The following is a detailed description of the new cultivar grown outdoors derived from evaluation rooted softwood cuttings grown in one gallon containers, two and three year-old specimens grown in 3 gallon containers, and multiple field grown specimens grown under different climactic conditions. All specimens were grown in Powell, Ohio, United States of America, under natural light conditions. The specimens have performed well in Zone 5b (−10 to −15 degrees F.) of the USDA Plant Hardiness Zone Map *Misc. Pub.* 1475 *Henry Cathey* January 1990. The new *Hibiscus* has been observed to do well in daytime temperatures up to 100 degrees F. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Jodi' is a cultivar of *Hibiscus syriacus.*

Parentage: *Hibiscus syriacus* 'Jodi' is a spontaneous naturally occurring genetic branch mutation cultivated genetic sport of *Hibiscus syriacus* 'Diana'.

Growth habit of the plant described as to the shape of the plant at maturity, and branching habit: 'Jodi' is a shrub or small tree with upright branching habit. At maturity, the plant has an upright oval shape.

Characteristics of the plant in winter dormancy: The winter habit is one of medium texture. The outline is a semi-broad upright oval shape.

Complete botanical description of bark, buds, blossoms, leaves, and fruit:

*Bark.*—Older bark is grey (RHS Grey Group 201-A) with semi-smooth texture. Younger stems have maroon color (RHS Greyed-Orange Group 166A) and are very smooth.

*Buds.*—Are not significant and are located by the leaf scars of the previous year.

*Blossoms.*—Flowers are generated on current year's growth. They are five petaled, perfect, solitary, single whorl (5.5-6.0 centimeters in length, approximately 5 centimeters in width, obovate shape, apex rounded to obtuse, margin entire and undulate, colored on both surfaces RHS Yellow-White Group 158D typically and observed to be approximately 4 centimeters in depth, and occur in August through September. The calyx is star shaped with five sepals. The sepals are narrowly deltoid in shape, the apex is acute, and the margin is entire, texture smooth, and length approximately 2 centimeters. The color on the upper and lower surfaces is RHS Yellow-Green Group 145A. The peduncle has a length of approximately 5-10 millimeters, a diameter of approximately 2.5 millimeters, and is RHS Yellow-Green Group 144B in color. The petiole has a diameter of approximately 2.0-2.5 millimeters and is RHS Yellow-Green Group 146 B in color. The flowers on this cultivar start a week later than other varieties but lasts much longer into the season. The flowers also remain open at night. The flowers of the parent plant are thought to be sterile and observation of *Hibiscus syriacus* 'Jodi' has generated no apparent self-seeding.

*Leaves.*—The leaves are alternately located on the stem. The leaves have three lobes with palmate venation. The leaf shape is ovate with a cuneate base with acute apices. The margins are fixed with rounded serrations. The leaves are 2 to 4 inches in length and 1¾ to 2½ inches in width at the widest point. The upper surface of the leaf has a waxy texture. The lower leaf surface is dull with minor pubescence along the venation. The petiole is ¼" to 1" in length, with a typical and observed diameter of approximately 2.0-2.5 mm and is RHS Yellow-Green Group 146 B in color. The leaf colors are best described using Royal Horticultural Society Color Charts. The leaves have three colors, consistent on both the upper and lower leaf surfaces. The darkest green is the same shade as RHS Fan3 137A. The light green is best described as RHS Fan3 138B. The yellow is best described as RHS Fan3 153C. The color pattern is irregular leaf by leaf. The variegation follows the venation in irregular unpredictable patterns.

*Fruit.*—The fruit is dehiscent five-valved capsule, approximately 2 centimeters in diameter. The fruit starts out a light green (RHS Yellow-Green Group 144A) about ¾" long. After the capsule opens, it turns brown (RHS Grey-Brown Group 199D) and persists through winter.

Plant characteristics: This *Hibiscus* has a medium growth rate. The plant has lateral branches, typically and observed to be approximately 30 centimeters in length, 4 millimeters in diameter, with an internodal length of between 2 and 4 centimeters, and RHS Greyed-Orange Group 166A in coloration. The flower bud is blunt in shape, barely evident, and obscured by leaf of fruit scars, with a length of 2 millimeters, a diameter of 3 millimeters, and RHS Orange-White Group 159A in coloration. The reproductive organs are as follows: Stamens: Anther length approximately 1 millimeter; anther color RHS Yellow Group 11B; pollen amount moderate; pollen color RHS Yellow Group 11B; pistal quantity per flower — one; length approximately 3 centimeters; stigma — round, five parted white RHS White Group 155D; style approximately 3 centimeters long, color RHS White Group 155D; ovary color RHS Greyed-Green Group 193B.

The ultimate height is 8'-12' in height and 6'-10' wide. The plant is hardy from zone 5 to zone 8. This particular cultivar has shown little if any self-seeding, which is a nuisance with many of the other cultivars. The flowers show no fragrance. This cultivar has shown no significant susceptibility to diseases or insects. The plant roots easily from softwood cuttings taken in June to July when treated with 1000 ppm IBA.

I claim:

1. A new and distinct cultivar of *Hibiscus* plant named 'Jodi' as herein illustrated and described.

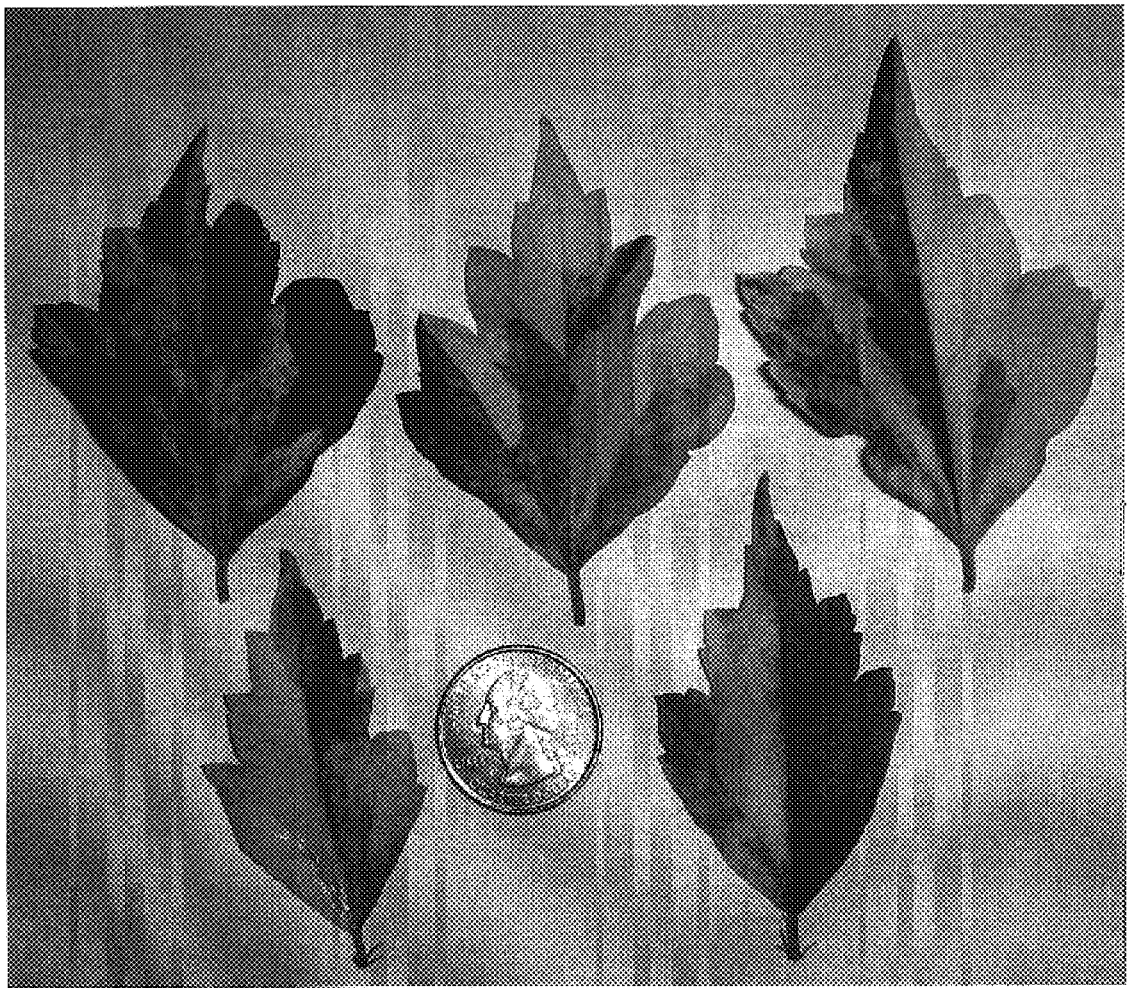

* * * * *